(12) United States Patent
Bruss

(10) Patent No.: US 12,708,553 B1
(45) Date of Patent: Aug. 18, 2026

(54) ADJUSTABLE MOUTHPIECE FOR SNORING AND TEETH GRINDING PREVENTION

(71) Applicant: Shinrin-Yoku Traders LLC, Sherwood, OR (US)

(72) Inventor: Ryan Bruss, Sherwood, OR (US)

(73) Assignee: SHINRIN-YOKU TRADERS LLC, Sherwood, OR (US)

( * ) Notice: Subject to any disclaimer, the term of this patent is extended or adjusted under 35 U.S.C. 154(b) by 0 days.

(21) Appl. No.: 19/427,769

(22) Filed: Dec. 19, 2025

Related U.S. Application Data

(60) Provisional application No. 63/775,686, filed on Mar. 21, 2025.

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ...... A61F 5/56; A61F 5/566; A61F 2005/563; A61C 7/36; A61C 7/08; A61C 5/90; A63B 71/085; A63B 2071/088; A63B 2071/086
USPC .................. 128/848, 859, 861–862; 433/6–7
See application file for complete search history.

(56) References Cited

U.S. PATENT DOCUMENTS 5,313,960 A * 5/1994 Tomasi .................. A61F 5/566 128/862
6,055,986 A 5/2000 Meade
8,684,006 B2 4/2014 Levendowski et al.
8,833,374 B2 9/2014 Fallon et al.
9,545,331 B2 1/2017 Ingemarsson-Matzen
D888,249 S 6/2020 Bruss
10,905,582 B2 2/2021 Newby et al.
11,357,662 B2 6/2022 Bruss
11,576,808 B2 2/2023 Gelb et al.
11,690,753 B2 7/2023 Newby et al.
11,998,478 B2 6/2024 Newby et al.
2010/0261133 A1 10/2010 Lax
2011/0017220 A1* 1/2011 Lindsay .................. A61F 5/566 128/848
2011/0226261 A1* 9/2011 Hernandez ............. A61F 5/566 128/848
2012/0041440 A1 2/2012 Tong et al.
2014/0352701 A1 12/2014 Ingemarsson-Matzen
2020/0222228 A1* 7/2020 Bruss ...................... A61F 5/566
(Continued)

FOREIGN PATENT DOCUMENTS

WO WO-2016027949 A1 * 2/2016 .............. A61F 5/01

OTHER PUBLICATIONS

Machine translation of WO2016027949A1 (Year: 2016).*

*Primary Examiner* — Caitlin A Carreiro
(74) *Attorney, Agent, or Firm* — INNOVATION CAPITAL LAW GROUP, LLP; Vic Lin

(57) ABSTRACT

A mouthpiece includes an upper mold including an upper teeth tray and a plurality of connection channels. The mouthpiece includes a lower mold including a lower teeth tray and a plurality of connection tabs. The plurality of connection channels are sized to allow the plurality of connection tabs to move within the plurality of connection channels. The mouthpiece includes a plug configured to be removably inserted between the upper mold and the lower mold.

20 Claims, 9 Drawing Sheets

(56) References Cited

U.S. PATENT DOCUMENTS

| | | | | |
|---|---|---|---|---|
| 2023/0310130 | A1* | 10/2023 | Collins, Jr. ............ | A61C 13/34<br>264/16 |
| 2025/0332024 | A1 | 10/2025 | Newby et al. | |

* cited by examiner 300
306
304
306

300
306
304
306

ADJUSTABLE MOUTHPIECE FOR SNORING AND TEETH GRINDING PREVENTION

CROSS-REFERENCE TO RELATED APPLICATIONS

This application claims priority to U.S. Application No. 63/775,686, filed Mar. 21, 2025, which is hereby incorporated by reference in its entirety.

FIELD OF INVENTION

The present disclosure relates to oral appliances for medical conditions, and more particularly to an adjustable mouthpiece designed to prevent snoring and teeth grinding.

BACKGROUND OF THE INVENTION

Mouthguards and mouthpieces are protective devices designed to fit over the teeth to help prevent injuries to the teeth, gums, and jaw. These devices are typically made of soft, flexible materials, such as rubber or plastic, and are commonly used in sports, especially contact sports like football, boxing, and hockey, to protect against trauma from impacts. Beyond sports applications, mouthguards and mouthpieces can also help address various medical conditions involving the mouth, such as teeth grinding (bruxism) and snoring during sleep.

Conventional mouthguards generally come in three main categories. Pre-formed mouthguards are manufactured in standard sizes and are ready to use when purchased, but may not fit users well because each person's mouth is unique. As such, pre-formed mouthguards may be less comfortable and provide less protection. Boil-and-bite mouthguards can be softened by boiling in water and then molded to the shape of the wearer's mouth. These mouthguards may offer a better fit than pre-formed options but are still somewhat bulkier than custom alternatives. Custom-made mouthguards are specifically designed by dental professionals to fit the exact shape of the user's teeth and mouth. While custom-made mouthguards may provide the best fit, comfort, and protection, they tend to be more expensive and require professional involvement.

Existing mouthpieces face several limitations in their construction and functionality. Conventional mouthpieces constructed of moldable plastics tend to wear through quickly and lack adjustability features. Mouthpieces constructed of a combination of moldable and hard plastics may offer improved durability but tend to be more bulky and less comfortable for users. Additionally, many conventional mouthpieces do not provide adequate customization options to accommodate the wide variety of mouth shapes and dental configurations found among different users.

SUMMARY OF THE INVENTION

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

According to an aspect of the present disclosure, a mouthpiece provided. The mouthpiece includes an upper mold comprising an upper teeth tray and a plurality of connection channels. The mouthpiece comprises a lower mold comprising a lower teeth tray and a plurality of connection tabs. The plurality of connection channels are sized to allow the plurality of connection tabs to move within the plurality of connection channels. The mouthpiece comprises a plug configured to be removably inserted between the upper mold and the lower mold.

According to another aspect of the present disclosure, a mouthpiece is provided. The mouthpiece includes an upper mold comprising an upper teeth tray, a plug slot, and a plurality of connection channels including a front connection channel and side connection channels. A lower mold comprises a lower teeth tray and a plurality of connection tabs including a front connection tab and side connection tabs. The plurality of connection channels are longer along their longitudinal axes than the corresponding connection tabs to allow sliding movement between the upper mold and the lower mold. A plug comprises a tab and legs extending from the tab. The legs are configured to extend through the plug slot to create an airway between the upper mold and the lower mold.

According to an aspect of the present disclosure, a method is provided. The method includes assembling a mouthpiece by coupling an upper mold to a lower mold through connection tabs engaging with connection channels and inserting a plug between the upper mold and the lower mold. The mouthpiece is placed in hot water for a predetermined time to soften thermoplastic material of the upper mold and the lower mold. The mouthpiece is placed in a user's mouth and having the user bite down to mold the upper mold and the lower mold to the user's teeth. The mouthpiece is removed from the user's mouth and placing the mouthpiece in cold water to fix the molded shape The foregoing general description of the illustrative embodiments and the following detailed description thereof are merely exemplary aspects of the teachings of this disclosure and are not restrictive.

BRIEF DESCRIPTION OF DRAWINGS

Non-limiting and non-exhaustive examples are described with reference to the following figures.

DETAILED DESCRIPTION OF THE PROFFERED EMBODIMENTS

The following description sets forth exemplary aspects of the present disclosure. It should be recognized, however, that such description is not intended as a limitation on the scope of the present disclosure. Rather, the description also encompasses combinations and modifications to those exemplary aspects described herein.

The present disclosure relates to an adjustable mouthpiece designed to address snoring and teeth-grinding conditions. The mouthpiece may comprise multiple interconnected components that work together to provide a customizable oral appliance. The adjustable nature of the mouthpiece may allow users to modify the relative positioning of components prior to a molding process, thereby accommodating various mouth shapes and dental configurations. The mouthpiece may include an upper component and a lower component that may be coupled together through a connection system. The connection system may allow controlled movement between the components while maintaining structural integrity during use. A removable element may be positioned between the upper and lower components to maintain an airway opening during the molding process. The components of the mouthpiece may be constructed from materials that exhibit both flexibility during molding and rigidity after cooling. This dual-phase material behavior may enable the mouthpiece to conform to individual dental structures while providing stable support during use. The adjustable features may accommodate different bite relationships and jaw positions without requiring multiple pre-formed sizes.

The following description sets forth the structural features and operational characteristics of the mouthpiece. The description may provide details regarding the individual components, their interconnection mechanisms, material properties, and methods of use. The structural arrangements and functional relationships described herein may enable the mouthpiece to serve as an effective oral appliance for addressing sleep-related breathing and dental grinding issues.

Figure 1:
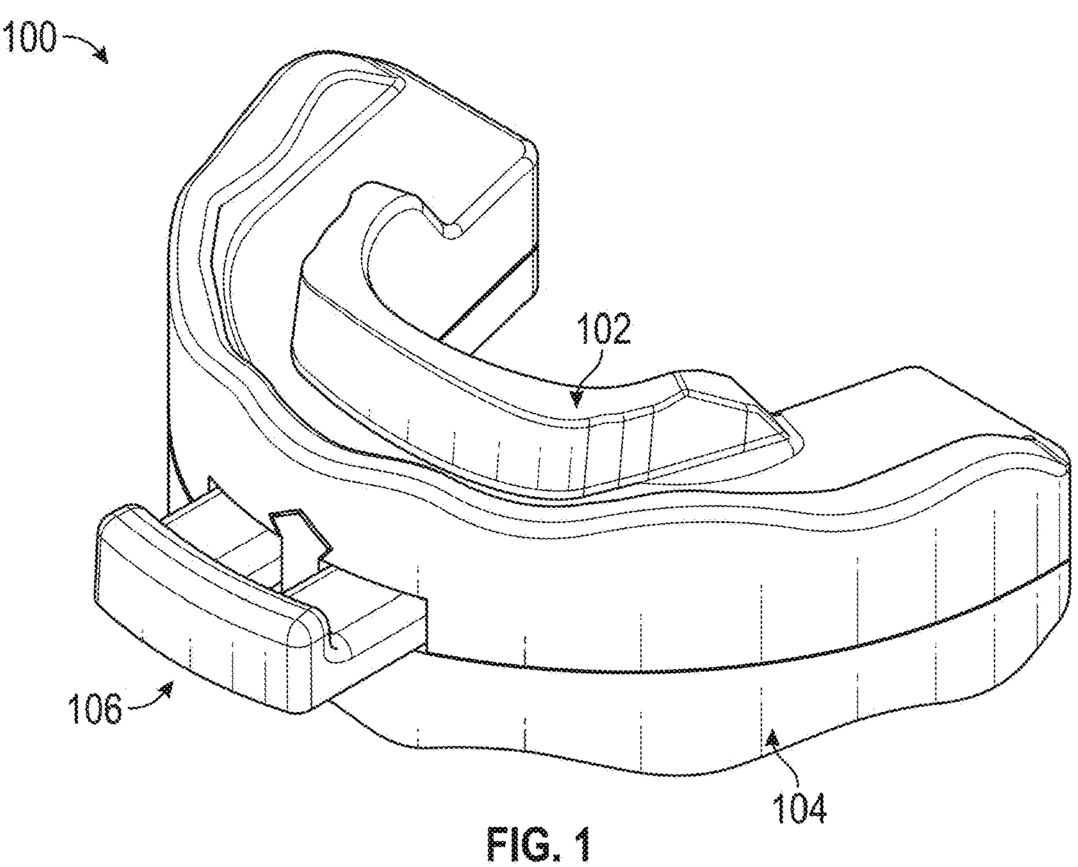
FIG. 1 is a top-perspective view of a mouthpiece with an upper mold, lower mold, and plug, according to aspects of the present disclosure.

Referring to FIG. 1, a mouthpiece 100 may comprise three main components that work together to form an adjustable oral appliance. The mouthpiece 100 may include an upper mold 102, a lower mold 104, and a plug 106. The upper mold 102 and the lower mold 104 may mate together to create a structure that may be received into a user's mouth for fitting and molding processes. The plug 106 may be positioned between the upper mold 102 and the lower mold 104 when the components are assembled.

The multi-piece design of the mouthpiece 100 may enable adaptation to different mouth sizes and configurations. The upper mold 102 and the lower mold 104 may move relative to one another prior to molding, thereby allowing the mouthpiece 100 to accommodate various mouth shapes. The adjustable positioning may address different dental conditions such as overbite or underbite configurations without requiring pre-formed sizing options. The upper mold 102 and the lower mold 104 may be constructed of ethylene vinyl acetate (EVA). EVA may be a thermoplastic material that exhibits moldable characteristics when heated and may be fixed into a rigid shape through cooling. The EVA construction may allow the upper mold 102 and the lower mold 104 to conform to individual dental structures during a molding process while providing stable support after the material has cooled and hardened. The plug 106 may be constructed of a rigid material such as polycarbonate (PC). The rigid construction of the plug 106 may allow the component to maintain structural integrity during the molding process. The plug 106 may create an airway between the upper mold 102 and the lower mold 104 during the molding process, thereby enabling breathing while the mouthpiece 100 is being fitted to a user's mouth. The plug 106 may be removed after the molding process has been completed.

Figure 2:
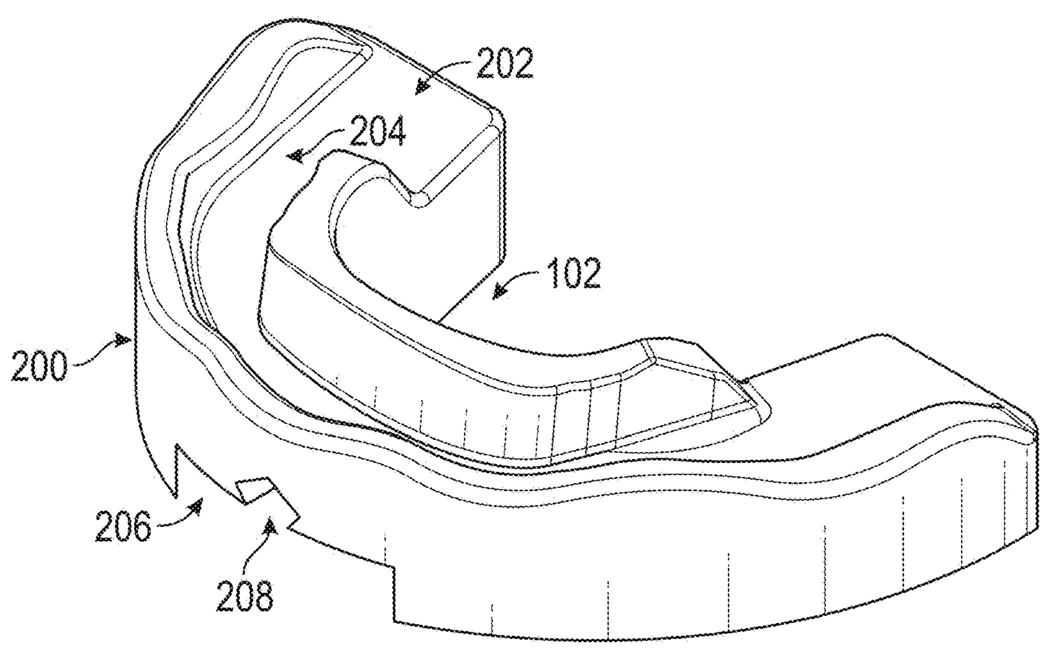
FIG. 2 is a top-perspective view of the upper mold of the mouthpiece, according to aspects of the present disclosure.

Referring to FIG. 2, the upper mold 102 may be viewed from a top-perspective orientation that reveals both structural surfaces and functional features of the component. The upper mold 102 may include a bottom surface 200 and a top surface 202 that serve different functions within the mouthpiece 100 assembly. The bottom surface 200 may abut the lower mold 104 when the upper mold 102 and the lower mold 104 are joined together to form the assembled mouthpiece 100. The top surface 202 may include an upper teeth tray 204 that may be configured to receive and mold to the upper teeth of a user. The upper teeth tray 204 may be shaped as a curved channel that follows the contour of a typical upper dental arch. During the molding process, the upper teeth tray 204 may conform to the specific shape of a user's upper teeth, gums, and mouth structure through the application of heat and pressure.

The bottom surface 200 may include a plug slot 206 and a front connection channel 208 that serve connection and airway functions within the mouthpiece 100. The plug slot 206 may be configured to receive the plug 106, thereby providing an airway between the upper mold 102 and the lower mold 104 during the molding process. The front connection channel 208 may be configured to receive a corresponding connection tab from the lower mold 104, thereby allowing the upper mold 102 and the lower mold 104 to be coupled together while permitting relative movement between the two components prior to molding.

Figure 3:
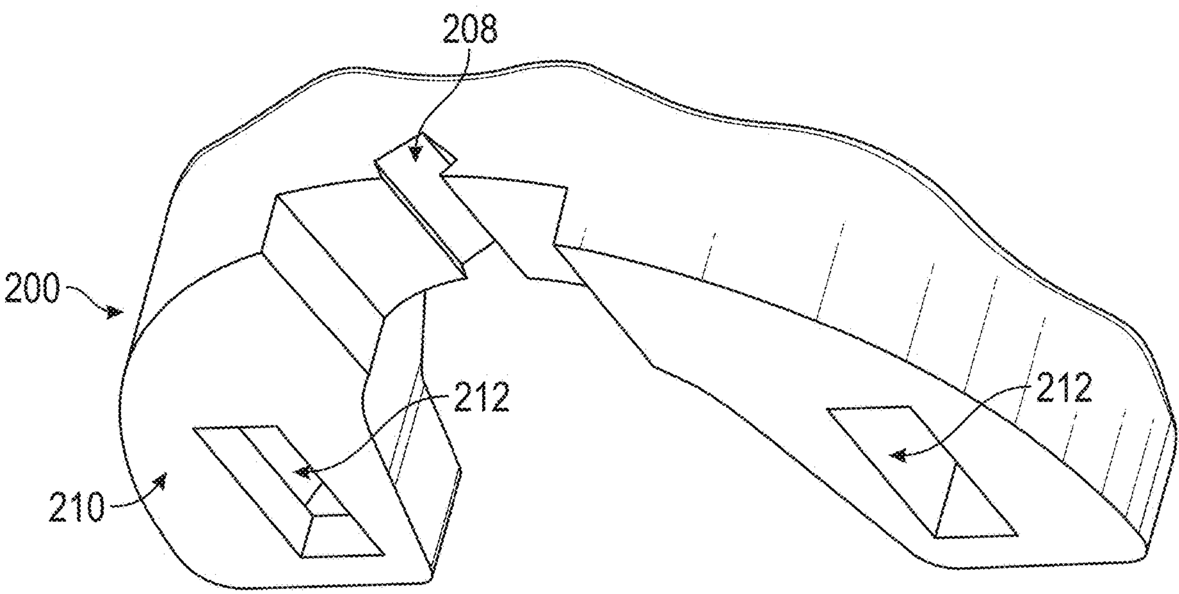
FIG. 3 is a bottom-perspective view of the upper mold of FIG. 2, according to aspects of the present disclosure.

Referring to FIG. 3, the upper mold 200 may be viewed from a bottom-perspective orientation that reveals connection features configured to interface with the lower mold 104. The bottom-perspective view may show connection channels that may receive connection tabs of the lower mold 104, thereby allowing the upper mold 200 and the lower mold 104 to move relative to one another for adaptation to different user mouth shapes. The bottom surface of the upper mold 200 may include the front connection channel 208 positioned at a front portion of the component. The front connection channel 208 may be configured to receive a front connection tab from the lower mold 104. The front connection channel 208 may have a diamond or triangular shape that may match the corresponding shape of the front connection tab. The diamond or triangular configuration may provide a secure connection while allowing controlled movement between the upper mold 200 and the lower mold 104.

The bottom surface of the upper mold 200 may also include side connection channels 212 positioned on lateral portions of the component. The side connection channels 212 may be configured to receive side connection tabs from the lower mold 104. The side connection channels 212 may be rectangularly shaped and may include a slanted lip on an outer edge of each channel. The slanted lip configuration may engage with hooks of the side connection tabs, thereby providing a secure connection mechanism between the upper mold 200 and the lower mold 104.

The front connection channel 208 and the side connection channels 212 may be dimensioned to be longer along their longitudinal axes than the corresponding connection tabs. The extended length of the connection channels may allow the connection tabs to move within the channels, thereby enabling the upper mold 200 to be moved relative to the lower mold 104 prior to molding. This adjustable positioning capability may accommodate different mouth shapes and bite relationships without requiring multiple pre-formed mouthpiece sizes.

An upper teeth tray 210 may be visible from the bottom-perspective view of the upper mold 200. The upper teeth tray 210 may form part of the curved channel structure that may receive and mold to the upper teeth of a user during the fitting process.

Figure 4:
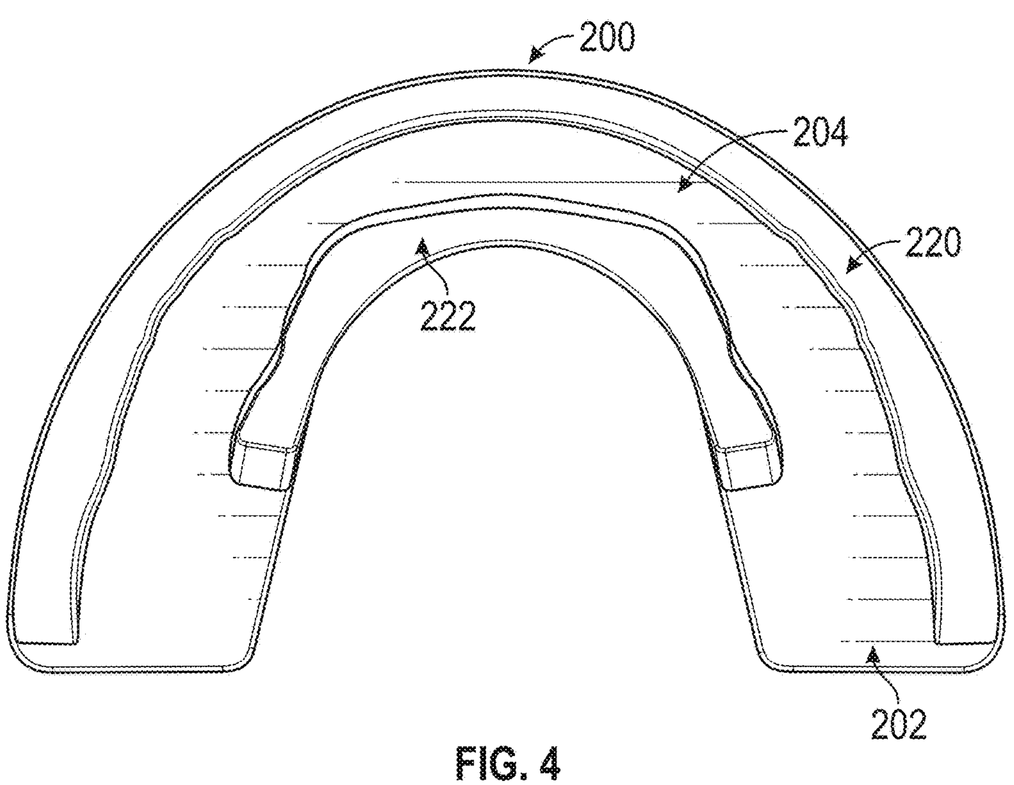
FIG. 4 is a top view of the upper mold of FIG. 2, according to aspects of the present disclosure.

Referring to FIG. 4, the upper mold 200 may be viewed from a top orientation that reveals the structural configuration of the upper teeth tray 204. The top surface 202 of the upper mold 200 may feature the upper teeth tray 204 in a detailed arrangement that may accommodate the natural positioning of upper teeth within a user's mouth. The upper teeth tray 204 may be shaped in a curved channel configuration that may correspond to the natural dental arch arrangement. The curved channel may follow an arch-shaped path that may match the typical arrangement of upper teeth in a user's mouth. This curved configuration may enable the upper teeth tray 204 to receive the upper teeth during the molding process and conform to the specific dental structure of individual users.

The upper teeth tray 204 may include an outer ridge 220 that may extend along the outer perimeter of the curved channel. The outer ridge 220 may be configured to mold to the outer surface of the teeth during the fitting process. The outer ridge 220 may provide a molding surface that may conform to the buccal and labial surfaces of the upper teeth when the mouthpiece 100 undergoes the thermal molding process.

The upper teeth tray 204 may also include an inner ridge 222 that may be positioned along the inner perimeter of the curved channel. The inner ridge 222 may be configured to mold to the inner surface of the teeth, specifically the lingual and palatal surfaces of the upper teeth. The inner ridge 222 may work in conjunction with the outer ridge 220 to create a comprehensive molding surface that may encompass both the inner and outer tooth surfaces.

The inner ridge 222 may be shortened in height relative to the outer ridge 220. This dimensional relationship between the inner ridge 222 and the outer ridge 220 may provide structural benefits during the molding and fitting process. The shortened configuration of the inner ridge 222 may allow for improved comfort and may accommodate variations in tongue positioning while maintaining effective molding contact with the inner tooth surfaces. The height differential between the outer ridge 220 and the inner ridge 222 may also facilitate easier insertion and removal of the mouthpiece 100 while providing adequate molding coverage for both inner and outer dental surfaces.

Figure 5:
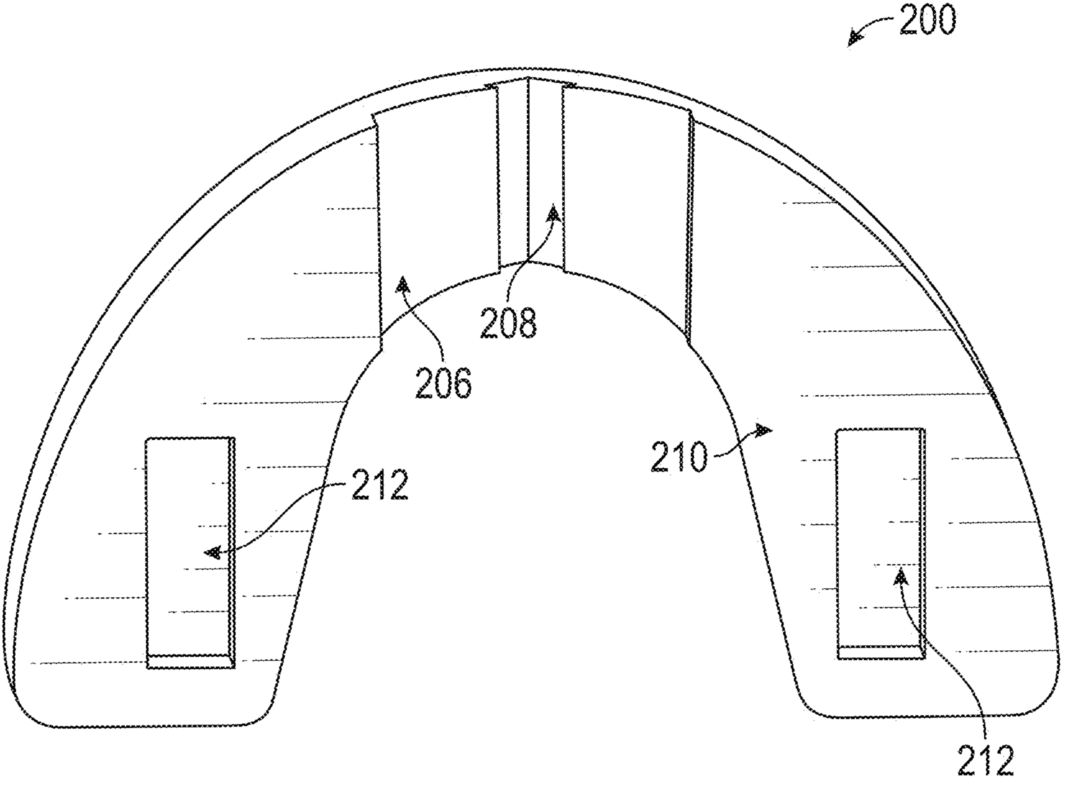
FIG. 5 is a bottom view of the upper mold of FIG. 2, according to aspects of the present disclosure.

Referring to FIG. 5, the upper mold 200 may be viewed from a bottom orientation that reveals the complete arrangement of connection features and internal passages within the component. The bottom view may show the structural elements that facilitate assembly with the lower mold 104 and accommodate the plug 106 during the molding process. The upper mold 200 may include a front connection channel 208 positioned at the front central portion of the component. The front connection channel 208 may have a diamond or triangular shape that may be configured to receive a correspondingly shaped connection tab from the lower mold 104. The diamond or triangular configuration may provide a secure mechanical connection while allowing controlled movement between the upper mold 200 and the lower mold 104 during adjustment procedures.

Side connection channels 212 may be located on either side of the upper mold 200, positioned toward the rear portions of the component. The side connection channels 212 may be rectangularly shaped and may include a slanted lip on the outer edge of each channel. The slanted lip configuration may engage with hooks of side connection tabs from the lower mold 104, thereby creating a secure connection mechanism that may resist separation while allowing relative movement between the components. The front connection channel 208 and the side connection channels 212 may be elongated along their longitudinal axes. The elongated configuration may provide a length greater than the corresponding connection tabs, thereby allowing relative movement between the upper mold 200 and the lower mold 104 during adjustment. This dimensional relationship may enable users to modify the positioning of the upper mold 200 relative to the lower mold 104 prior to the molding process, thereby accommodating different mouth shapes and bite relationships.

The plug slot 206 may extend through the center of the upper mold 200, forming an opening that may run from the front to the rear of the mold body. When the plug 106 is inserted into the plug slot 206, the plug 106 may maintain an airway opening between the upper mold 200 and the lower mold 104 during the molding process. The airway opening may enable breathing while the mouthpiece 100 is positioned in a user's mouth during the thermal molding procedure.

The upper teeth tray 210 may be visible from the bottom view as a curved channel structure that may define the space for receiving and molding to the upper teeth of a user. The curved channel structure may complement the connection features and plug slot 206 to create a comprehensive molding system that may accommodate individual dental structures while maintaining airway access during the fitting process.

Figures 6, 7:
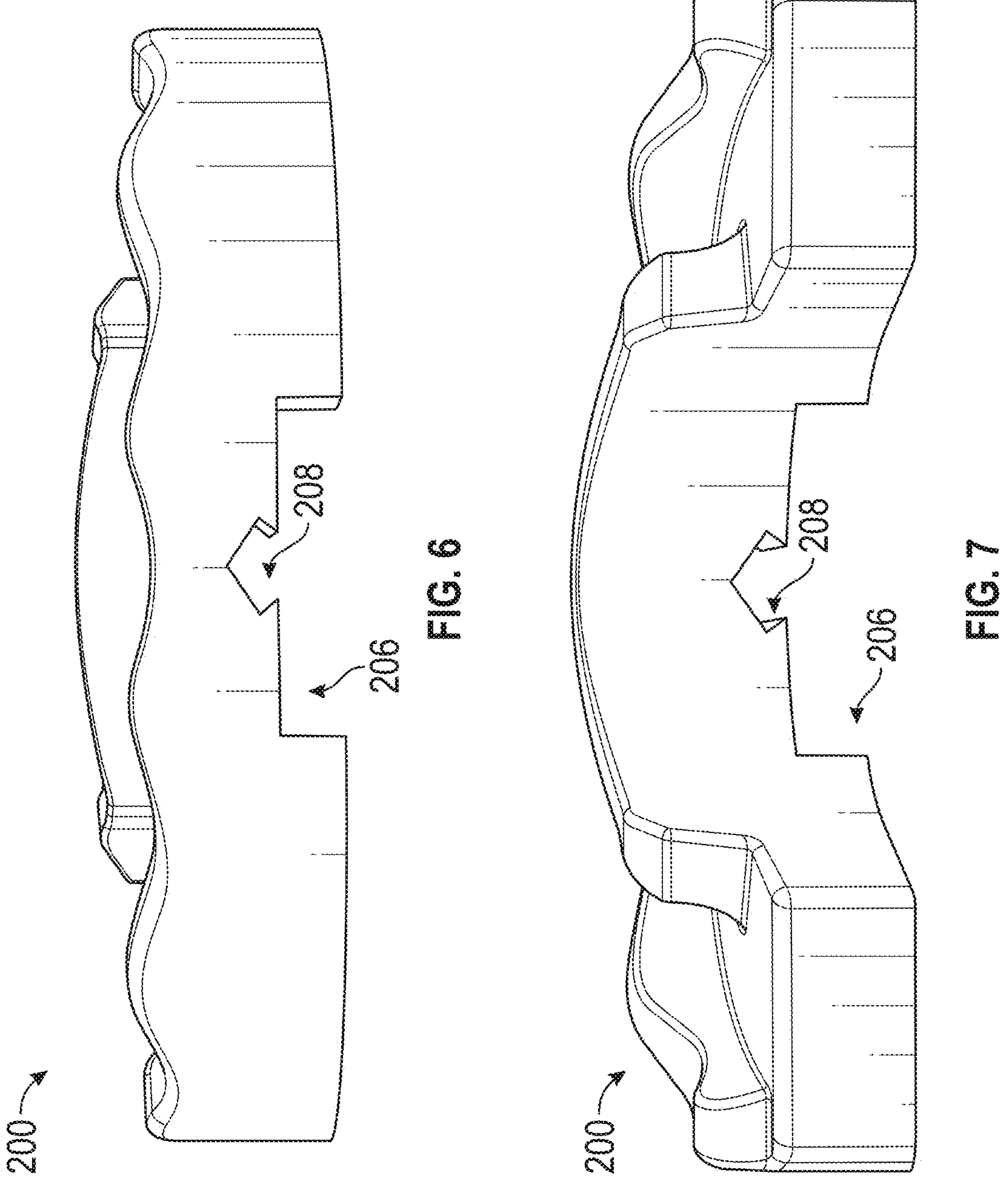
FIG. 6 is a front view of the upper mold of FIG. 2, according to aspects of the present disclosure.
FIG. 7 is a front view of the upper mold of FIG. 2, according to aspects of the present disclosure.

Referring to FIG. 6 and FIG. 7, the upper mold 200 may be viewed from a front and rear orientations that reveal the structural arrangement of connection and airway features as they appear from the frontal perspective. The plug slot 206 opening can be seen to extend from the front face to the rear face of the upper mold 200 to enable airflow when the mouthpiece 100 is assembled and positioned within a user's mouth. Similarly, the configuration of the front connection channel 208 can be seen as consistent from the front face to the rear face of the upper mold 200. The front connection channel 208 may be configured to receive a corresponding front connection tab from the lower mold 104, thereby facilitating the mechanical coupling between the upper mold 200 and the lower mold 104. The diamond or triangular shape of the front connection channel 208 may be apparent from the front perspective, showing the geometric configuration that may match the corresponding connection tab shape.

Figure 8:
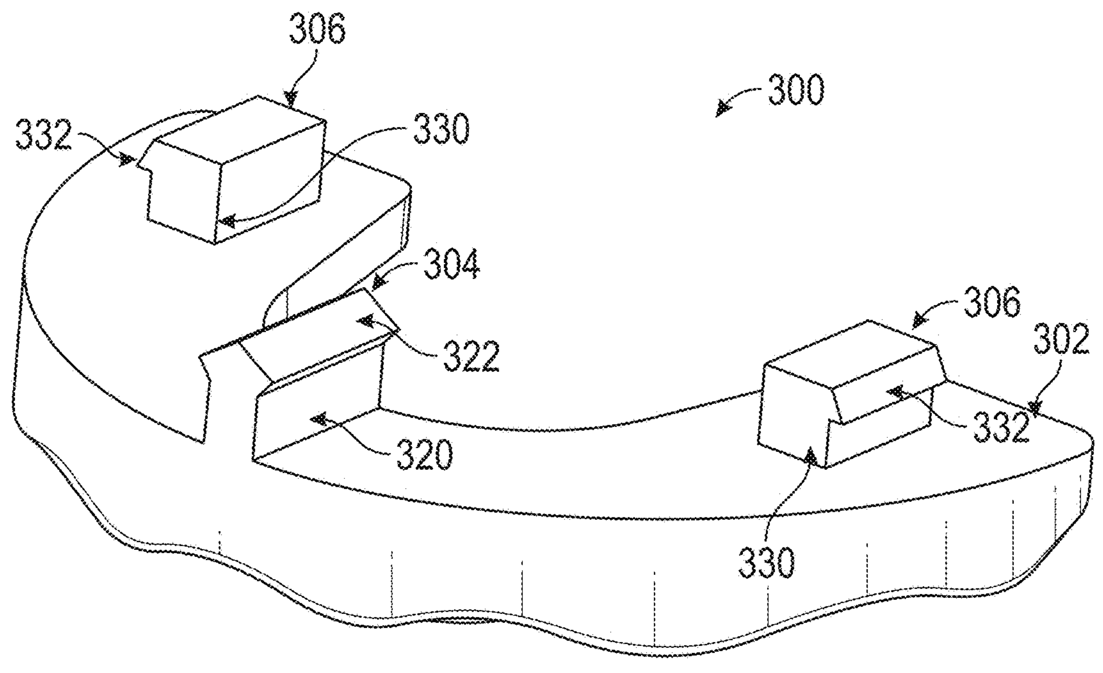
FIG. 8 is a top-perspective view of the lower mold of the mouthpiece, according to aspects of the present disclosure.

Referring to FIG. 8, the lower mold 300 may be viewed from a top-perspective orientation that reveals the connection features configured to interface with the upper mold 102. The lower mold 300 may include a top surface 302 that may abut the upper mold 102 when the components are joined together to form the assembled mouthpiece 100.

The top surface 302 may include a front connection tab 304 positioned at a front portion of the lower mold 104. The front connection tab 304 may comprise a post 320 extending from the top surface 302 and a head 322 at a distal end of the post 320. The post 320 may provide a structural connection between the top surface 302 and the head 322, thereby creating a projecting element that may engage with the front connection channel 208 of the upper mold 102. The head 322 may be diamond or rectangular shaped to match the corresponding shape of the front connection channel 208. The diamond or rectangular configuration of the head 322 may provide a secure mechanical connection while allowing controlled movement between the lower mold 104 and the upper mold 102 during adjustment procedures.

The top surface 302 may also include side connection tabs 306 positioned on lateral portions of the lower mold 104. The connection tabs 306 may mate with the corresponding connection channels 212 of the upper mold 102, thereby enabling the upper mold 102 and the lower mold 300 to move relative to one another for adaptation to different user mouth shapes. The side connection tabs 306 may each include a post 330 and a hook 332 at a distal end of the post 330. The post 330 may extend from the top surface 302 to provide structural support for the hook 332. The hook 332 may be adapted to engage with the lip of the side connection channels 212 of the upper mold 102, thereby creating a secure connection mechanism between the lower mold 104 and the upper mold 102.

The hooks 332 may be faced outward, thereby placing tension on the outer edges of the corresponding side connection channels 212. This outward orientation of the hooks 332 may create a tensioned connection that may resist inadvertent movement between the upper mold 102 and the lower mold 104 during handling. Users may reduce the tension by applying pressure to the sides of the mouthpiece 100, which may assist in adjusting the relative positioning of the upper mold 102 and the lower mold 104. The pressure application may temporarily relieve the tension created by the hooks 332, thereby enabling easier adjustment of the component positioning prior to the molding process.

The connection tabs (304 and 306) may be sized to allow movement within the corresponding connection channels (208 and 212) of the upper mold 102, thereby enabling the upper mold 102 and the lower mold 104 to move relative to one another prior to molding. This adjustable positioning capability may accommodate different mouth shapes and bite relationships without requiring multiple pre-formed mouthpiece sizes.

Figure 9:
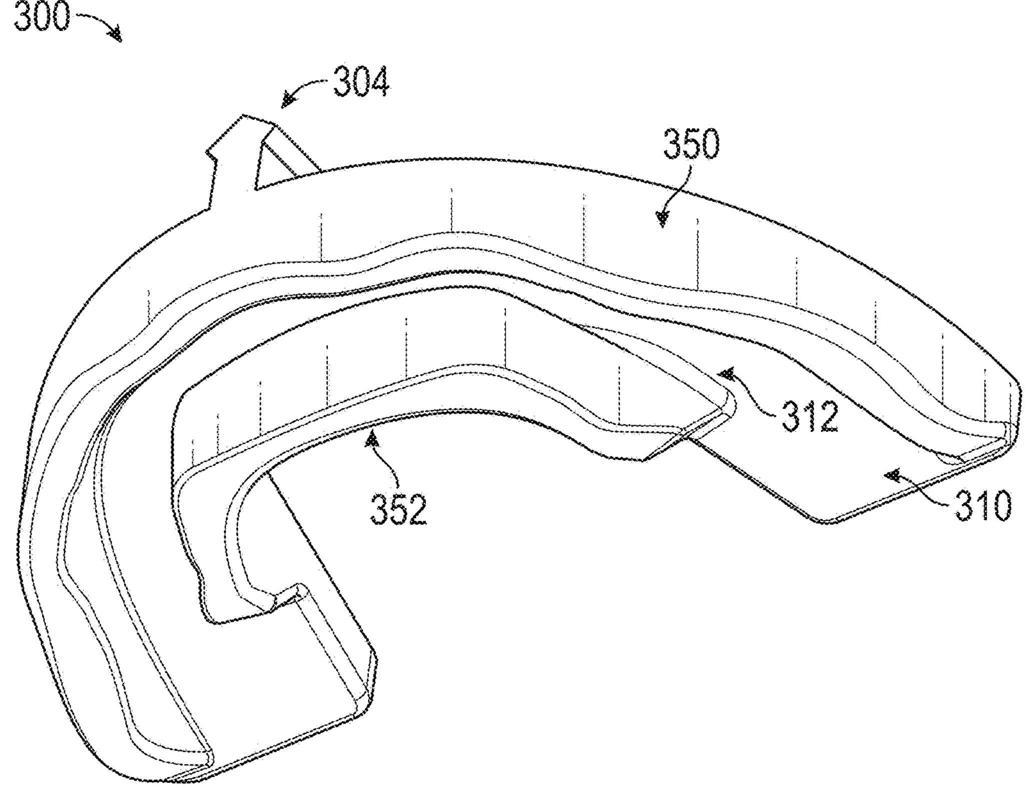
FIG. 9 is a bottom-perspective view of the lower mold of FIG. 8, according to aspects of the present disclosure.
Figures 10, 11:
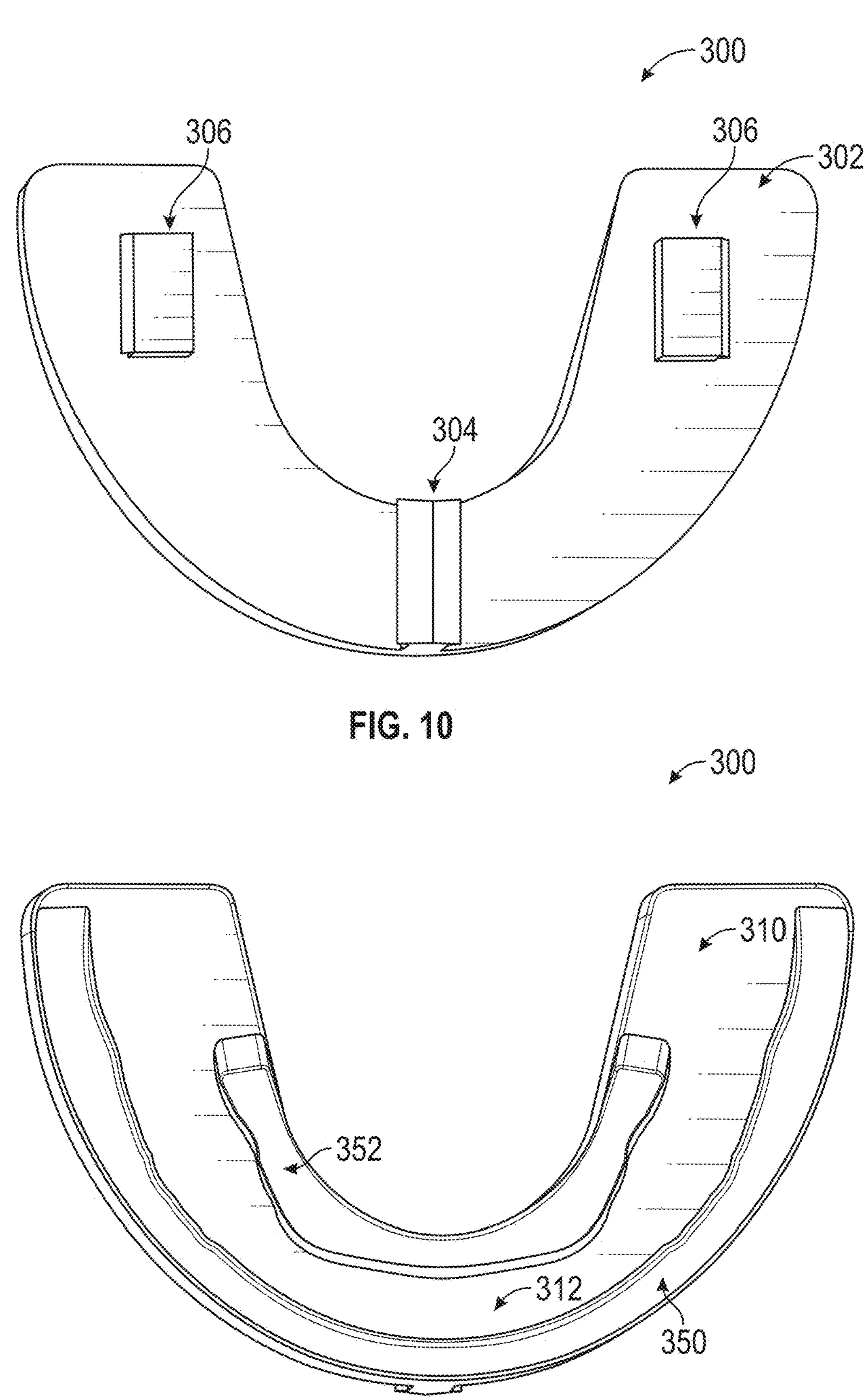
FIG. 10 is a top view of the lower mold of FIG. 8, according to aspects of the present disclosure.
FIG. 11 is a bottom view of the lower mold of FIG. 8, according to aspects of the present disclosure.

Referring now to FIG. 9 FIG. 11, the lower mold 300 is shown according to an embodiment. The lower mold 300 may include a bottom surface 310 that may face downward when the mouthpiece 100 is assembled and positioned within a user's mouth. The bottom surface 310 may serve as the primary molding interface for the lower dental structure during the fitting process. The bottom surface 310 may include a lower teeth tray 312 that may be configured to receive and mold to the shape of the lower teeth of a user. The lower teeth tray 312 may be formed within the bottom surface 310 and may be shaped as a curved channel that may follow the contour of a typical lower dental arch. The curved channel configuration may enable the lower teeth tray 312 to accommodate the natural arrangement of lower teeth within a user's mouth during the molding process.

The lower teeth tray 312 may include an outer ridge 350 that may extend [0055] along the outer perimeter of the curved channel structure. The outer ridge 350 may be configured to mold to the outer surface of the lower teeth during the thermal fitting process. The outer ridge 350 may provide a molding surface that may conform to the buccal and labial surfaces of the lower teeth when the mouthpiece 100 undergoes the heating and molding procedure. The outer ridge 350 may work in conjunction with other structural elements of the lower teeth tray 312 to create a comprehensive molding interface for the lower dental structure.

The lower teeth tray 312 may also include an inner ridge 352 that may extend along the inner perimeter of the curved channel structure. The inner ridge 352 may be configured to mold to the inner surface of the lower teeth, specifically the lingual surfaces of the lower teeth that face toward the tongue. The inner ridge 352 may complement the outer ridge 350 to provide molding contact with both the inner and outer surfaces of the lower teeth during the fitting process.

The inner ridge 352 may be shorter in height relative to the outer ridge 350. This dimensional relationship between the inner ridge 352 and the outer ridge 350 may provide structural and functional benefits during the molding and use of the mouthpiece 100. The shortened configuration of the inner ridge 352 may allow for improved comfort during wear by providing additional space for tongue movement and positioning. The height differential may also facilitate easier insertion and removal of the mouthpiece 100 while maintaining adequate molding coverage for the inner surfaces of the lower teeth. The reduced height of the inner ridge 352 may accommodate variations in tongue positioning and oral anatomy while providing effective molding contact with the lingual surfaces of the lower teeth.

The front connection tab 304 may be visible extending from the top surface of the lower mold 300 in the bottom-perspective view. The lower mold 300 may be constructed of a flexible and malleable material, such as ethylene vinyl acetate (EVA), that may allow the lower teeth tray 312 to be molded to the specific shape of a user's lower teeth, gums, and mouth structure through the application of heat and pressure during the thermal molding process.

The front connection tab 304 and the side connection tabs 306 may be dimensioned to be shorter along their longitudinal axes than the corresponding connection channels in the upper mold 102. This dimensional relationship may allow the connection tabs to move within the connection channels, thereby enabling the upper mold 102 to be moved relative to the lower mold 104 prior to molding. The shorter length of the connection tabs relative to the connection channels may create a sliding mechanism that may permit adjustment of the relative positioning between the upper mold 102 and the lower mold 104.

The adjustable positioning capability may accommodate different mouth shapes and bite relationships that may occur in various users. The sliding mechanism may enable the mouthpiece 100 to address different dental conditions such as overbite configurations, where the upper teeth may extend beyond the lower teeth, and underbite configurations, where the lower teeth may extend beyond the upper teeth. The adjustable nature of the connection system may allow users to modify the relative positioning of the upper mold 102 and the lower mold 104 to match their specific dental alignment prior to the molding process.

The adjustment mechanism may provide a continuous range of adjustment positions rather than being limited to fixed increments or predetermined positions. The sliding connection between the connection tabs and the connection channels may allow for infinite positioning within the range of movement permitted by the dimensional relationship between the tabs and channels. This continuous adjustment capability may enable precise customization of the mouthpiece 100 to match individual dental structures and bite relationships without requiring selection from a limited number of pre-formed sizes or configurations. The continuous range of adjustment may provide enhanced fitting flexibility compared to systems that may offer only discrete adjustment positions or fixed sizing options.

The lower teeth tray 312 may include structural features that may facilitate comprehensive molding contact with the lower teeth during the thermal fitting process. The curved channel may provide molding surfaces that may conform to both the outer and inner surfaces of the lower teeth when the ethylene vinyl acetate material is heated and shaped. The molding surfaces may adapt to the specific contours of individual teeth within the lower dental arch, creating a customized interface that may provide effective contact with the dental structure.

The configuration of the lower teeth tray 312 may allow the lower mold 300 to conform not only to the teeth but also to the surrounding gum tissue and mouth shape during the molding process. The curved channel structure may extend to accommodate the gingival areas adjacent to the teeth, thereby creating a molding interface that may encompass both the dental and periodontal structures. This comprehensive molding capability may enable the lower mold 300 to create a stable and comfortable fit that may address both the teeth and the surrounding oral tissues.

The natural arch configuration of the lower teeth tray 312 may facilitate proper positioning of the lower mold 300 within a user's mouth during the molding process. The curved channel may guide the placement of the lower teeth within the molding interface, thereby ensuring proper alignment between the dental structure and the molding surfaces. The arch-shaped configuration may provide anatomical reference points that may assist in achieving correct positioning of the mouthpiece 100 during the thermal fitting procedure.

Figures 12, 13:
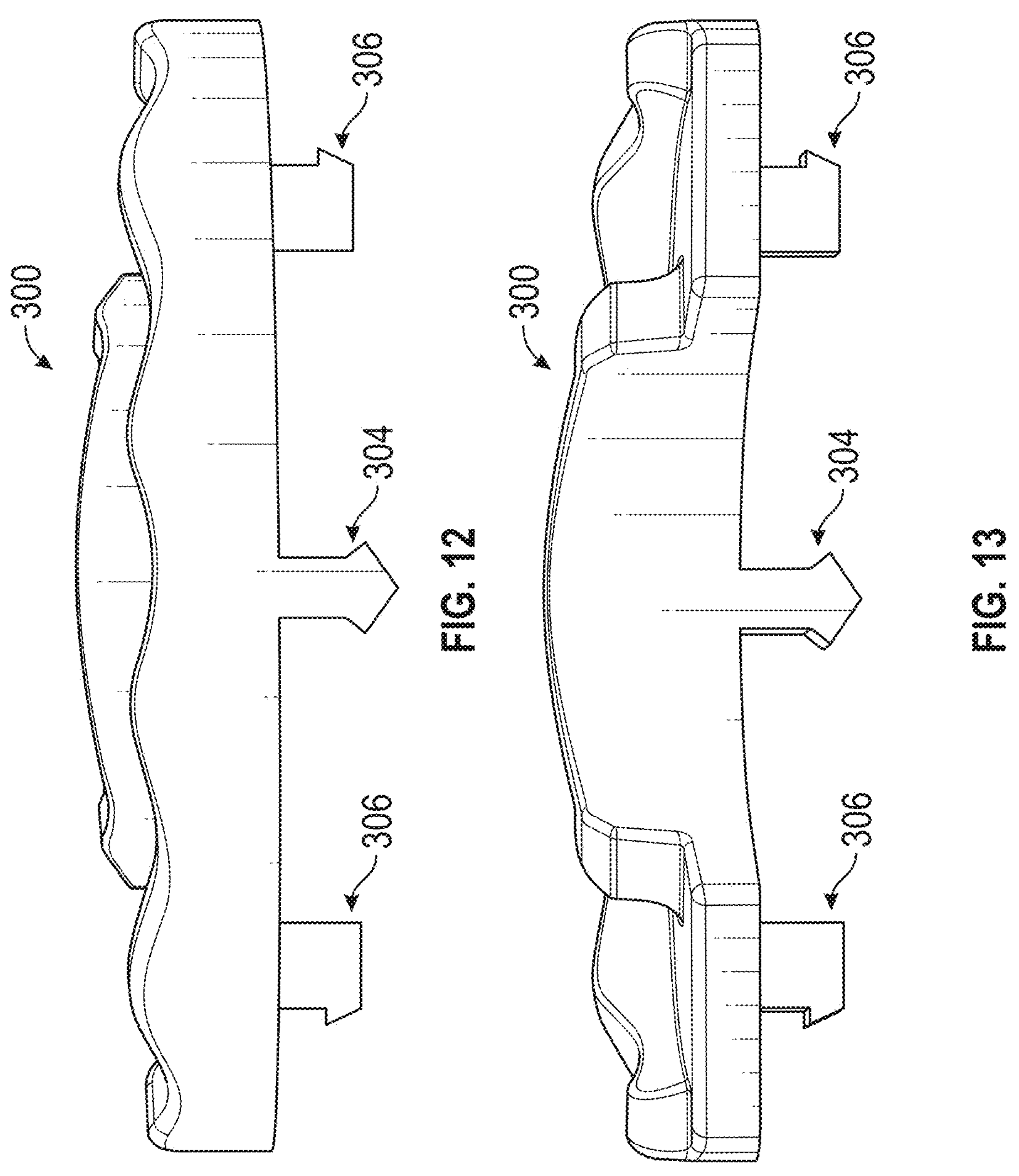
FIG. 12 is a front view of the lower mold of FIG. 8, according to aspects of the present disclosure.
FIG. 13 is a front view of the lower mold of FIG. 8, according to aspects of the present disclosure.

Referring now to FIG. 12 and FIG. 13, the lower mold 300 may be viewed from the front and rear orientations to reveal the structural arrangement of connection features as they appear from the frontal and rear perspectives. The front view may show the connection tabs positioned on the top surface of the lower mold 300, including the front connection tab 304 and the side connection tabs 306 that may be configured to interface with the corresponding connection channels of the upper mold 102. The front connection tab 304 may be visible extending from the top surface of the lower mold 300 in the front view orientation. The front connection tab 304 may be positioned centrally at the front portion of the lower mold 300, creating a projecting element that may engage with the front connection channel 208 of the upper mold 102. The diamond or triangular-shaped head of the front connection tab 304 may be apparent, showing the geometric configuration that may provide mechanical coupling between the lower mold 300 and the upper mold 102.

The side connection tabs 306 may be positioned on either side of the lower mold 300, extending from the top surface and visible from the front view orientation. The side connection tabs 306 may include posts that may extend upward from the top surface of the lower mold 300, with hooks positioned at the distal ends of the posts. The hooks may be configured to engage with the lips of the side connection channels 212 in the upper mold 102, thereby creating a secure connection mechanism between the components.

The connection tabs may be shaped to match the corresponding connection channels of the upper mold 102, thereby providing secure coupling between the molds while maintaining the capability for relative movement during adjustment procedures. The geometric compatibility between the connection tabs and the connection channels may enable the mechanical coupling system to function effectively while allowing controlled movement between the upper mold 102 and the lower mold 300 prior to the molding process.

The secure coupling capability of the connection system may resist inadvertent separation between the upper mold 102 and the lower mold 300 during handling and use, while the movement capability may enable intentional adjustment of the relative positioning between the components. The connection tabs may engage with the connection channels in a manner that may provide structural stability during the molding process while allowing controlled movement when adjustment forces are applied to the mouthpiece 100.

The connection features visible from both the front and rear perspectives may demonstrate the comprehensive nature of the connection system that may extend throughout the lower mold 300. The consistent positioning and configuration of the connection tabs may provide multiple points of engagement with the upper mold 102, thereby creating a stable and adjustable connection mechanism that may accommodate different mouth shapes and bite relationships through the sliding adjustment capability.

In some cases, the upper mold and the lower mold may include identically shaped teeth trays that may provide interchangeable functionality between the components. The identical shaping of the teeth trays may enable the upper mold to serve as the lower mold and the lower mold to serve as the upper mold during the molding and fitting process. This interchangeable configuration may eliminate the need for component-specific positioning during assembly and use of the mouthpiece.

Identically shaped teeth trays may include the same curved channel configuration, ridge arrangements, and dimensional characteristics in both the upper mold and the lower mold. The outer ridges and inner ridges of both teeth trays may have matching heights, widths, and curvature profiles that may accommodate dental structures regardless of whether the component is positioned as an upper mold or a lower mold. The identical shaping may ensure that either component may provide effective molding contact with either upper or lower teeth during the thermal fitting process.

The interchangeable nature of the molds may allow the mouthpiece to be placed in a user's mouth in any orientation to mold the teeth. Users may position either mold component against either the upper teeth or the lower teeth without concern for component-specific orientation requirements. This flexibility may simplify the fitting process by eliminating the need to identify and correctly position upper-specific and lower-specific components during assembly and molding procedures.

The interchangeable configuration may provide manufacturing and inventory benefits by reducing the number of distinct components required for the mouthpiece system. A single mold design may serve both upper and lower functions, thereby simplifying production processes and reducing the complexity of component management. The identical shaping may also provide user convenience by eliminating the possibility of incorrect component orientation during assembly and use.

The identical teeth tray configuration may maintain the adjustable positioning capability between the molds regardless of their orientation within the user's mouth. The connection system may function effectively whether the components are positioned in their traditional upper and lower orientations or in reversed orientations. The sliding mechanism and connection features may accommodate the interchangeable positioning while maintaining the ability to adjust the relative positioning between the components prior to molding.

The interchangeable functionality may enhance the versatility of the mouthpiece by accommodating different user preferences and fitting approaches. Some users may find certain orientations more comfortable during the molding process, and the interchangeable configuration may allow for such preferences without compromising the effectiveness of the molding and fitting procedure. The identical shaping may ensure consistent molding performance regardless of the chosen orientation of the components.

Figure 14:
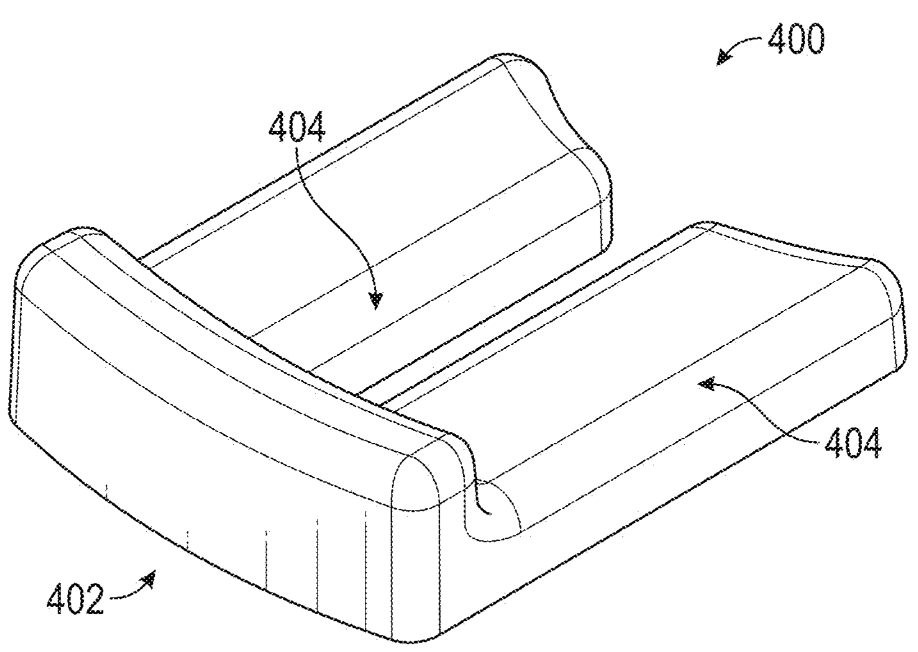
FIG. 14 is a top-perspective view of the plug of the mouthpiece, according to aspects of the present disclosure.
Figure 15:
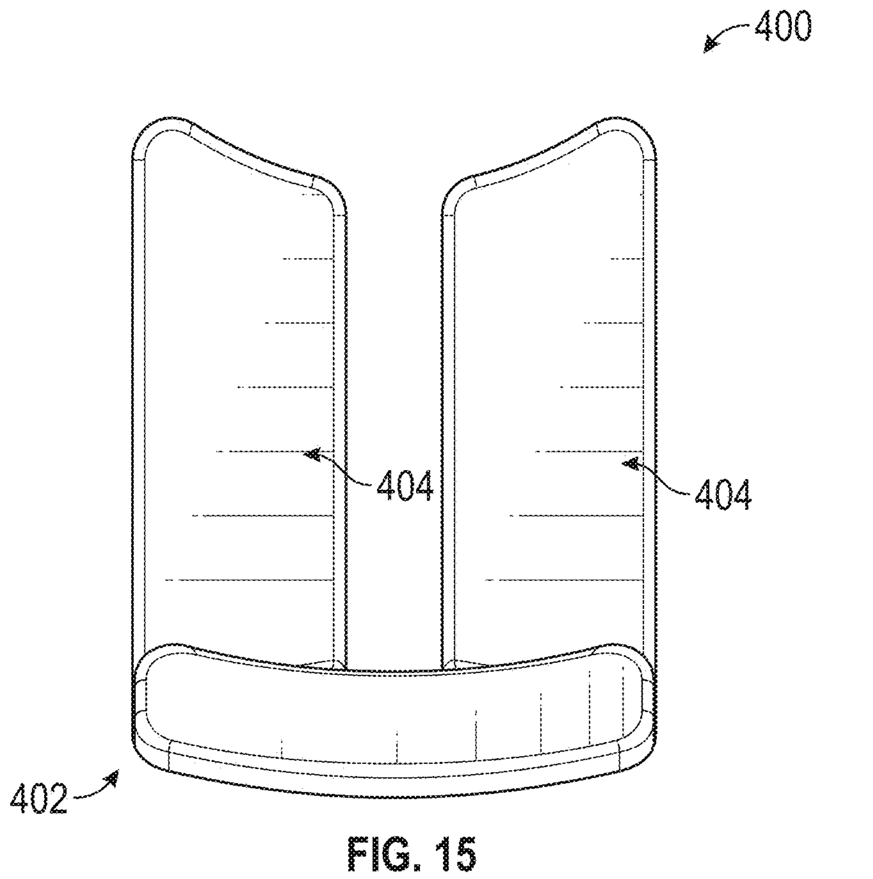
FIG. 15 is a top view of the plug of FIG. 14, according to aspects of the present disclosure.
Figure 16:
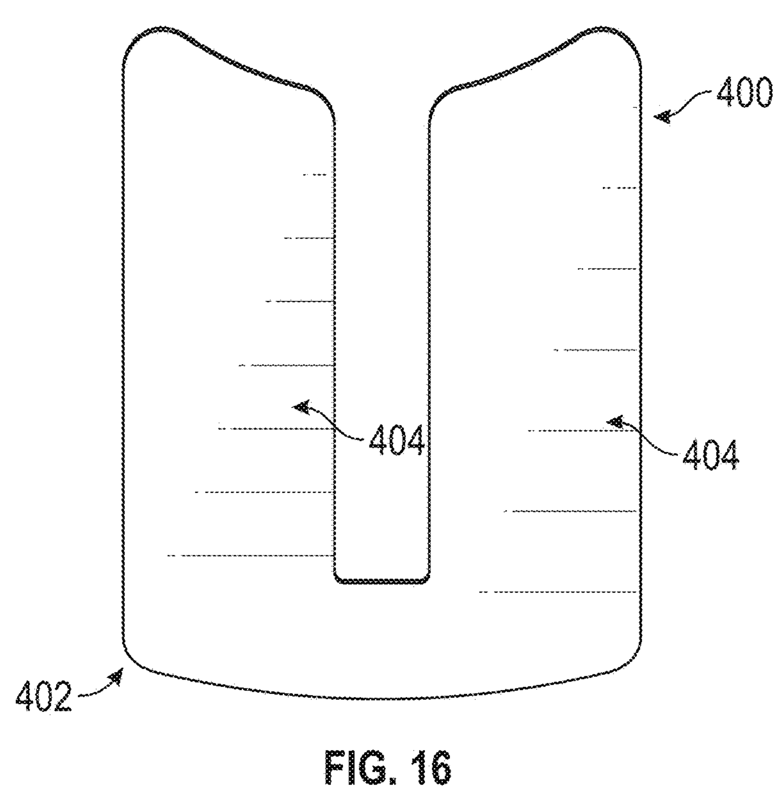
FIG. 16 is a bottom view of the plug of FIG. 14, according to aspects of the present disclosure.

Referring to FIG. 14-FIG. 16, a plug 400 is shown according to an embodiment (which may be similar to the plug 106 shown in FIG. 1). The plug 400 may include a tab 402 and legs 404 that may work together to provide airway maintenance functionality while enabling insertion and removal of the plug 400 from the mouthpiece 100 assembly. The tab 402 may be positioned at a front portion of the plug 400 and may serve as a gripping surface for inserting and removing the plug 400 from between the upper mold 102 and the lower mold 104. The tab 402 may provide a user-accessible interface that may facilitate handling of the plug 400 during assembly and disassembly procedures. The gripping surface configuration of the tab 402 may enable users to grasp and manipulate the plug 106 without interfering with the airway-forming function of the legs 404.

The legs 404 may extend from a rear surface of the tab 402 in an approximately parallel orientation relative to one another. The parallel configuration of the legs 404 may provide structural stability and may ensure consistent airway formation when the plug 400 is inserted into the mouthpiece 100. The legs 404 may be rectangular shaped with curved distal ends that may facilitate insertion into the plug slot 206 while providing smooth contact surfaces that may minimize discomfort during the molding process.

The rectangular shape of the legs 404 may provide structural integrity while maintaining a profile that may fit within the plug slot 206 of the upper mold 102. The curved distal ends of the legs 404 may reduce sharp edges and may provide a more comfortable interface when the plug 400 is positioned within a user's mouth during the molding procedure. The curved configuration may also facilitate easier insertion and removal of the legs 404 through the plug slot 206 during assembly and disassembly of the mouthpiece 100.

The legs 404 may be configured to be inserted through the plug slot 206 to create an airway between the upper mold 102 and the lower mold 104 during the molding process. When the legs 404 are positioned through the plug slot 206, the legs 404 may maintain a separation between the upper mold 102 and the lower mold 104 that may enable airflow through the assembled mouthpiece 100. The airway created by the legs 404 may provide respiratory access while the mouthpiece 100 is positioned within a user's mouth during the thermal molding procedure.

The legs 404 may be longer than the plug slot 206, thereby allowing the upper mold 102 and the lower mold 104 to be moved relative to one another while maintaining the airway during adjustment procedures. The extended length of the legs 404 relative to the plug slot 206 may accommodate the sliding movement between the upper mold 102 and the lower mold 104 without compromising the airway function. The dimensional relationship between the legs 404 and the plug slot 206 may enable the adjustable positioning capability of the mouthpiece 100 while ensuring continuous airway access throughout the range of adjustment positions.

The longer length of the legs 404 may ensure that the airway remains open regardless of the relative positioning between the upper mold 102 and the lower mold 104 during the adjustment process. As users modify the positioning of the molds to accommodate their specific mouth shape and bite relationship, the legs 404 may continue to provide airway separation between the components. The extended length may prevent airway obstruction that might otherwise occur if the legs 404 were dimensioned to match the plug slot 206 length exactly.

Figure 17:
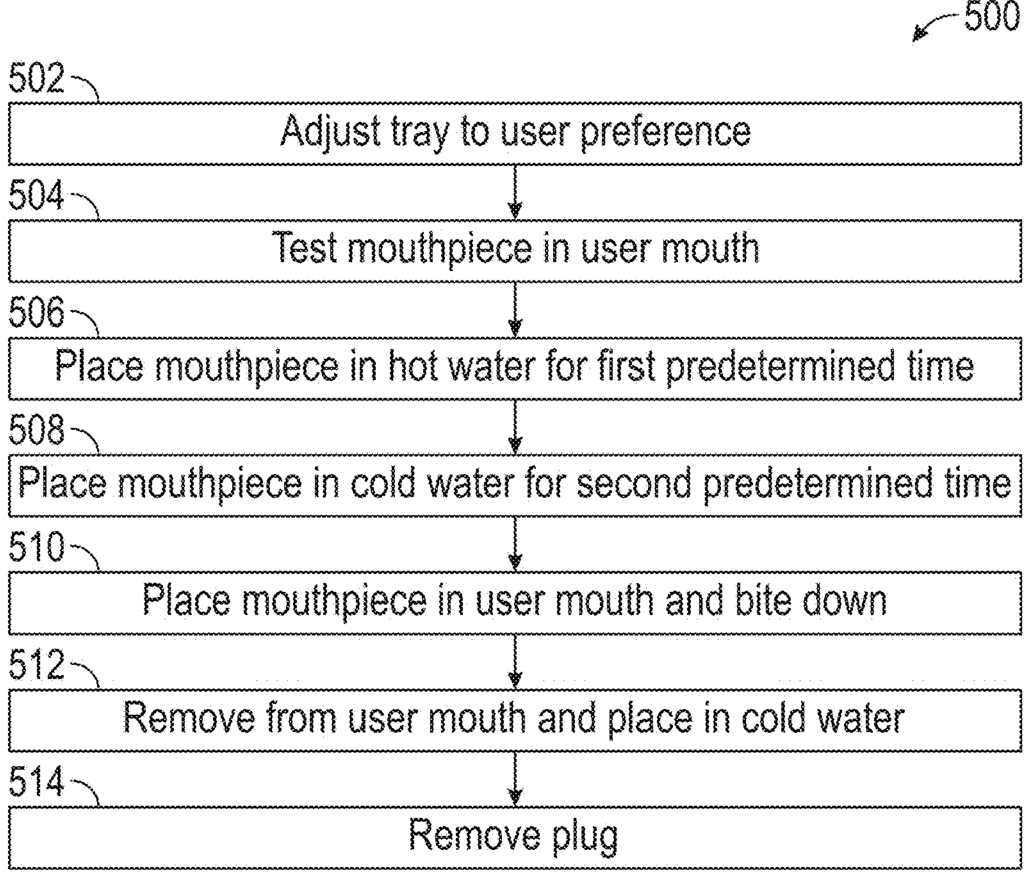
FIG. 17 is a flowchart for a method of using the mouthpiece, according to aspects of the present disclosure.

Referring to FIG. 17, a method 500 may be provided for using the mouthpiece 100 to create a customized oral appliance through a sequential molding and fitting process. The method 500 may comprise a series of steps that may enable the mouthpiece 100 to be molded to fit a user's mouth through controlled temperature changes and physical molding procedures. The method 500 may utilize the adjustable features of the mouthpiece 100 in combination with thermal molding techniques to create a customized fit for individual dental structures.

The method 500 may begin with a step 502 in which the user adjusts one of the trays of the mouthpiece 100 to the user's preferred fit. For example, the user may shift the relative positioning of the upper mold 102 and the lower mold 104 to accommodate the user's specific mouth shape and bite relationship prior to the molding process by pushing the upper mold 102 forward or backward relative to the lower mold 104, or vice versa.

Following assembly, the method 500 may proceed to a step 504 in which the mouthpiece 100 is tested in the user's mouth. During the step 504, the assembled mouthpiece 100 may be positioned within the user's mouth to evaluate the fit and positioning of the components. The testing step may enable verification that the upper teeth tray 204 and the lower teeth tray 312 are properly aligned with the user's dental structure. The step 504 may also allow for final adjustments to the relative positioning between the upper mold 102 and the lower mold 104 before proceeding with the thermal molding process. The airway created by the plug 106 may enable breathing during the testing step while the mouthpiece 100 is positioned within the user's mouth. The user may readjust the relative positioning of the upper mold 102 to the lower mold 104 until a comfortable fit is reached.

The method 500 may then advance to a step 506 in which the mouthpiece 100 is placed in hot water for a predetermined amount of time. During the step 506, the mouthpiece 100 may be placed in hot water for approximately 45 seconds. The hot water application may heat the ethylene vinyl acetate materials of the upper mold 102 and the lower mold 104, thereby causing the materials to become soft and malleable for the molding process. The heating duration of approximately 45 seconds may provide sufficient thermal energy to soften the thermoplastic materials while avoiding excessive heating that might compromise the structural integrity of the components. The plug 106 may remain rigid during the heating process due to the non-malleable characteristics of the polycarbonate construction.

Following the heating step, the method 500 may proceed to a step 508 in which the mouthpiece 100 is placed in cold water for a second predetermined time. During the step 508, the mouthpiece 100 may be placed in cold water for approximately 1 second. The brief cold water application may provide a controlled cooling phase that may prepare the heated mouthpiece 100 for insertion into the user's mouth. The approximately 1 second duration may reduce the temperature of the mouthpiece 100 to a level that may be comfortable for oral insertion while maintaining the malleable characteristics of the thermoplastic materials needed for the molding process.

The method 500 may then advance to a step 510 in which the mouthpiece 100 is placed in the user's mouth and the user bites down. During the step 510, the heated and briefly cooled mouthpiece 100 may be positioned within the user's mouth, and the user may bite down to engage the upper teeth with the upper teeth tray 204 and the lower teeth with the lower teeth tray 312. The user may press the mouthpiece 100 on all sides during the step 510, thereby molding the softened thermoplastic materials to conform to the specific shape of the user's teeth, gums, and mouth structure. The pressing action may ensure comprehensive contact between the molding surfaces and the dental structure, creating a customized fit that may address the individual characteristics of the user's oral anatomy.

The biting and pressing actions during the step 510 may cause the outer ridge 220 and the inner ridge 222 of the upper teeth tray 204 to conform to the outer and inner surfaces of the upper teeth. Similarly, the outer ridge 350 and the inner ridge 352 of the lower teeth tray 312 may conform to the outer and inner surfaces of the lower teeth. The molding process may accommodate the specific positioning, alignment, and contours of individual teeth within the user's dental arches. The airway maintained by the plug 106 may enable breathing during the molding process while the thermoplastic materials are being shaped to the user's dental structure.

The method 500 may conclude with a step 512 in which the mouthpiece 100 is removed from the user's mouth and placed in cold water. During the step 512, the molded mouthpiece 100 may be placed in cold water for approximately 5 minutes to fix the mold. The extended cold water application may cause the thermoplastic materials to cool and harden, thereby fixing the molded shape and creating a rigid structure that may retain the customized fit achieved during the molding process. The approximately 5 minute duration may provide sufficient cooling time to ensure complete hardening of the ethylene vinyl acetate materials and stabilization of the molded configuration.

The sequential molding and fitting process provided by the method 500 may enable customization of the mouthpiece 100 to individual dental structures through controlled temperature changes and physical molding procedures. The heating step may soften the thermoplastic materials to enable molding, while the brief initial cooling step may prepare the mouthpiece 100 for comfortable oral insertion. The molding step may allow the softened materials to conform to the user's specific dental structure through biting and pressing actions. The final cooling step may fix the molded configuration, creating a customized oral appliance that may provide effective contact with the user's teeth and mouth structure.

After the step 512 has been completed and the mouthpiece 100 has been removed from the cold water, the plug 106 may be removed (step 514). The removal and disposal of the plug 106 may complete the customization process, leaving behind the formed airway passage within the completed mouthpiece 100. The discarding of the plug 106 may eliminate the rigid component that was needed during the molding process, resulting in a finished oral appliance that may be worn by the user to address snoring and teeth-grinding conditions. The completed mouthpiece 100 may retain the customized fit achieved through the method 500 while providing the adjustable positioning benefits that were established during the assembly and adjustment phases of the process.

Disclaimers

Terms such as "top," "bottom," "front," "rear," "above," "below" and the like as used in this disclosure should be understood as referring to an arbitrary frame of reference, rather than to the ordinary gravitational frame of reference. Thus, for example, an item disposed above another item may be located above or below the other item along a vertical, horizontal or diagonal direction; and an item disposed below another item may be located below or above the other item along a vertical, horizontal or diagonal direction. Some frames of references and the position of claimed structure relative to those frames of reference may be gleaned from the appended drawings. Yet, it should be understood that for some embodiments, the detection from devices disclosed herein may not be restricted to being accomplished from any particular position shown, whether the device is above, below, or on one side of the user being monitored.

Those of skill in the art would appreciate that various components and blocks may be arranged differently (e.g., arranged in a different order, or partitioned in a different way) all without departing from the scope of the subject technology. The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects.

Thus, the claims are not intended to be limited to the aspects shown herein, but are to be accorded the full scope consistent with the language of claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

The invention claimed is:

1. A mouthpiece, comprising:

an upper mold comprising an upper teeth tray, a plug slot, and a plurality of connection channels including a front connection channel and side connection channels having a slanted lip on an outer edge;

a lower mold comprising a lower teeth tray and a plurality of connection tabs including a front connection tab and side connection tabs, the side connection tabs having posts and hooks at distal ends of the posts, wherein the hooks are configured to engage with the slanted lip of the side connection channels and place tension on outer edges of the side connection channels, wherein the plurality of connection channels are longer along their longitudinal axes than corresponding connection tabs to allow sliding movement between the upper mold and the lower mold; and a plug comprising a tab and legs extending from the tab, wherein the legs are configured to extend through the plug slot to create an airway between the upper mold and the lower mold.

2. The mouthpiece of claim 1, wherein the front connection tab comprises a post extending from a top surface of the lower mold and a head at a distal end of the post.

3. The mouthpiece of claim 2, wherein the hooks are configured to engage with the slanted lip of the side connection channels and place tension on outer edges of the side connection channels.

4. The mouthpiece of claim 3, wherein the tension can be reduced by applying pressure to sides of the mouthpiece to assist in adjusting the upper mold and the lower mold.

5. The mouthpiece of claim 1, wherein the upper mold and the lower mold are constructed of ethylene vinyl acetate (EVA).

6. The mouthpiece of claim 1, wherein the plug is constructed of polycarbonate.

7. The mouthpiece of claim 1, wherein the front connection channel has a diamond shape and the side connection channels have a rectangular shape with a slanted lip on an outer edge.

8. A mouthpiece apparatus, comprising:

an upper mold comprising an upper teeth tray configured to receive upper teeth of a user, a plug slot extending through the upper mold, and a plurality of connection channels including side connection channels having a slanted lip on an outer edge;

a lower mold comprising a lower teeth tray configured to receive lower teeth of the user and a plurality of connection tabs configured to engage with the plurality of connection channels, the plurality of connection tabs including side connection tabs having posts and hooks at distal ends of the posts, wherein the hooks are configured to engage with the slanted lip of the side connection channels and place tension on outer edges of the side connection channels, wherein the plurality of connection channels are configured to allow the plurality of connection tabs to move within the plurality of connection channels to enable relative positioning between the upper mold and the lower mold; and a plug comprising a tab and legs extending from the tab, wherein the legs are configured to extend through the plug slot to create an airway between the upper mold and the lower mold.

9. The mouthpiece apparatus of claim 8, wherein the upper teeth tray comprises an outer ridge configured to mold to an outer surface of the upper teeth and an inner ridge configured to mold to an inner surface of the upper teeth.

10. The mouthpiece apparatus of claim 9, wherein the inner ridge is shorter in height relative to the outer ridge.

11. The mouthpiece apparatus of claim 8, wherein the upper mold and the lower mold are constructed of ethylene vinyl acetate (EVA).

12. The mouthpiece apparatus of claim 8, wherein the plug is constructed of a rigid material configured to maintain structural integrity during a molding process.

13. The mouthpiece apparatus of claim 8, wherein the legs of the plug are longer than the plug slot to allow the upper mold and the lower mold to be moved relative to one another while maintaining the airway.

14. A mouthpiece, comprising:

an upper mold comprising an upper teeth tray and a plurality of connection channels including side connection channels having a slanted lip on an outer edge;

a lower mold comprising a lower teeth tray and a plurality of connection tabs, the plurality of connection tabs including side connection tabs having posts and hooks at distal ends of the posts, wherein the hooks are configured to engage with the slanted lip of the side connection channels and place tension on outer edges of the side connection channels, wherein the plurality of connection channels are sized to allow the plurality of connection tabs to move within the plurality of connection channels; and a plug configured to be removably inserted between the upper mold and the lower mold.

15. The mouthpiece of claim 14, wherein the plug is constructed of a rigid material.

16. The mouthpiece of claim 15, wherein the rigid material is polycarbonate.

17. The mouthpiece of claim 14, wherein the plurality of connection tabs comprises:

a front connection tab having a post extending from a top surface of the lower mold and a head at a distal end of the post; and side connection tabs having posts and hooks at distal ends of the posts.

18. The mouthpiece of claim 17, wherein the hooks are configured to engage with the slanted lip of the side connection channels and place tension on outer edges of the side connection channels.

19. The mouthpiece of claim 14, wherein the upper mold and the lower mold are constructed of ethylene vinyl acetate (EVA).

20. The mouthpiece of claim 14, wherein the plurality of connection channels comprises:

a front connection channel having a diamond shape; and side connection channels having a rectangular shape with a slanted lip on an outer edge.

* * * * *